United States Patent [19]

Buret et al.

[11] Patent Number: 5,540,224
[45] Date of Patent: Jul. 30, 1996

[54] DRUG DELIVERY PORT ENDOTRACHEAL TUBE

[75] Inventors: Anne M. Buret, Maryland Heights, Mo.; Pam Jablenski, Fort Edward, N.Y.; Robert A. Virag, Chesterfield, Mo.

[73] Assignee: Mallinckrodt Medical, Inc., St. Louis, Mo.

[21] Appl. No.: 86,526

[22] Filed: Jul. 1, 1993

[51] Int. Cl.$^6$ ................................................. A61M 16/00
[52] U.S. Cl. ........................ 128/207.14; 128/280.18; 128/207.15; 128/912; 604/280
[58] Field of Search .............................. 128/207.14, 911, 128/912, 207.15, 200.26, 200.18; 604/280

[56]  References Cited

U.S. PATENT DOCUMENTS

| | | | |
|---|---|---|---|
| 3,964,488 | 6/1976 | Ring et al. | 128/107.14 |
| 4,669,463 | 6/1987 | McConnell | 128/207.14 |
| 4,739,756 | 4/1988 | Horn | 128/207.14 |
| 4,787,894 | 11/1988 | Turnbull | 128/207.14 |
| 4,821,714 | 4/1989 | Smelser | 128/207.15 |
| 5,333,608 | 8/1994 | Cummins | 128/207.14 |
| 5,447,152 | 9/1995 | Kohsai et al. | 128/207.15 |

Primary Examiner—Stephen Funk
Assistant Examiner—V. Srivastava
Attorney, Agent, or Firm—David A. Hey

[57]  ABSTRACT

The present invention relates to endotracheal tubes used for conducting gases or vapors along the trachea, for example by an anesthesiologist, paramedic or emergency room doctor. In particular, the present invention relates to an improved and novel endotracheal tubes having structure which enables the simultaneous administration of medication to both lungs of the patient.

1 Claim, 3 Drawing Sheets

SECTION A-A

SECTION B-B

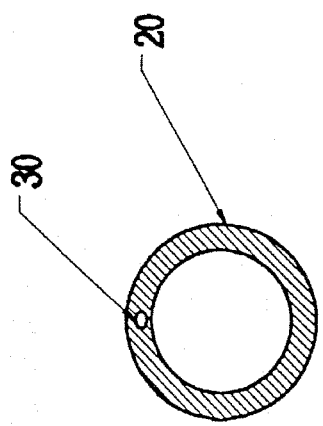
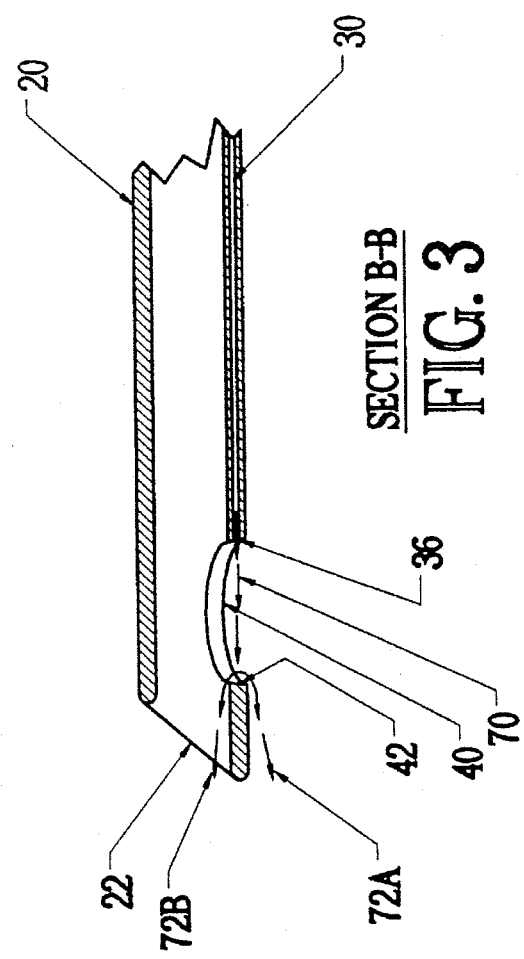

DRUG DELIVERY PORT ENDOTRACHEAL TUBE

BACKGROUND OF THE INVENTION

The present invention relates to endotracheal tubes used for conducting gases or vapors along the trachea, for example by an anesthesiologist, during the administration of anesthesia to patients undergoing surgery. In particular, the present invention relates to endotracheal tubes having means which enables the simultaneous administration of medication to both lungs of the patient during anesthesia. In addition, the endotracheal tubes according to the present invention are particularly useful for the paramedic in the field or the emergency room doctor, especially for the delivery of cardiac drugs.

Endotracheal tubes are generally used for anesthesia of a patient during surgery. Such endotracheal tubes may be introduced to the patient either orally or nasally. The endotracheal tube generally comprises a hollow tube made of a suitable plastic material, and which may be preferable pre-shaped so as to correspond to the patients pharynx and trachea. The endotracheal tube is inserted through the mouth or nose of the patient and extends along the patient's trachea.

It is often desirable to administer therapeutic drugs or agents directly to the lungs of the patient via an intubated endotracheal tube. Medications administered to the lungs in this manner are quickly taken up by the pulmonary (lung) vasculature and absorbed into the circulatory system.

Also, paramedics and emergency room doctors must often use endotracheal tubes to quickly intubate and apply mechanical ventilation to patients. It is often desirable to administer cardiac drugs through the intubated endotracheal tube directly to the lungs. Preferable, the cardiac drugs are distributed over as wide an area of the lungs as possible to optimally deliver the drugs to the circulatory system of the patient.

In general, drugs are delivered to a patient intravenously (IV). However, when venous access is difficult because of anatomy, trauma or disease, or in emergency situations, it is necessary to deliver drugs by another means, such as through an intubated endotracheal tube.

When the drugs or agents are to be delivered through an endotracheal tube, the generally accepted technique for administering such agents is to inject the agents into the proximal end of the endotracheal tube, and then "blowing" the drug down the tube into the lungs. However, there are several disadvantages to this method, including the need to interrupt ventilation during injection of the agent. In addition, it is difficult to measure the amount of agent actually delivered to the lungs, because the agent may be absorbed by secretions collected in the endotracheal tube, or may simply adhere to the walls of the endotracheal tube. Also, it is often desirable to atomize the agent during delivery, so as to provide better clinical results. Such atomization requires relatively high air flow, which can create other disadvantages. Finally, delivery through the main tube of the endotracheal tube makes it extremely difficult to administer the agent to both lungs of the patient, because the drug will generally flow through the distal end of the endotracheal tube and be administered to only one lung. It should be noted that a portion of the administered drug will often be expelled through the proximal end of the endotracheal tube upon exhalation by the patient.

Atomizing and delivery of the drug to both lungs of the patient is very important from a clinical standpoint. In particular, better clinical results can often be obtained by delivering smaller particles of the drug because the drug can then travel further into the small airways and alveolar surfaces. This allows the drug to spread out further and makes the kinetics approach that of IV delivery.

There have been several endotracheal tubes designed in an attempt to provide means of delivering drugs or agents through an endotracheal tube, which overcome the disadvantages noted above.

In particular, U.S. Pat. No. 4,584,998 to McGrail describes a multipurpose tracheal tube which may include up to three additional lumens formed within the wall of the main lumen. One of the additional lumens may be an insufflation lumen used to deliver humidified and atomized gasses to the patient. By providing an additional lumen, ventilation does not have to be discontinued, and metering of the agent delivered is simplified.

U.S. Pat. No. 4,669,463 to McConnell shows an endotracheal tube including a auxiliary lumen formed in the wall of the main lumen. The auxiliary lumen may be used to deliver liquid medicant to the distal end of the endotracheal tube.

U.S. Pat. No. 4,821,714 to Smelser is directed to an endotracheal tube having a primary lumen for delivery of ventilation gasses and a second lumen for administration of medication to the lungs of a patient. Smelser particularly describes an embodiment wherein the second lumen is branched and terminates at two outlets, one at the distal tip of the tube and the other along the exterior wall of the tube.

However, none of the prior art endotracheal tubes provide means for easily and effectively delivering medicant to the lungs of the patient, and more particularly to both lungs of the patient simultaneously.

OBJECTS OF THE PRESENT INVENTION

It is one object of the present invention to provide a tracheal tube which includes a medicant delivery lumen which allows the effective administration of pharmacologic agents or therapeutic drugs directly and simultaneously to both lungs of the patient.

Other objects of the present invention will be evident from the following discussion.

SUMMARY OF THE PRESENT INVENTION

The above objects are accomplished according to the present invention by providing a novel endotracheal tube having a secondary lumen which terminates at a perforation, such as a Murphy eye, formed through the wall of the main lumen. By providing such a secondary lumen, the endotracheal tube of the present invention allows for the administration of a pharmacologic agent or therapeutic drug directly and simultaneously to both lungs of the patient.

In particular, the secondary lumen of the endotracheal tube according to the present invention is provided in such a manner that medicant or other agents are delivered as a single stream exiting at the proximal side of the terminal opening, the stream then impacting the distal edge of the terminal opening thereby splitting the stream and delivering a portion of the medicant both internally and externally of the endotracheal tube. The diverted stream is thereby administered to both lungs of the patient simultaneously.

BRIEF DESCRIPTION OF THE DRAWINGS

FIG. 2 is a cross-sectional view of an endotracheal tube according to one embodiment of the present invention taken along section A—A of FIG. 1.

FIG. 3 is an expanded cross-sectional view of the distal end of an endotracheal tube according to the present invention taken along section B—B of FIG. 1.

DETAILED DESCRIPTION OF THE INVENTION

Figure 1:
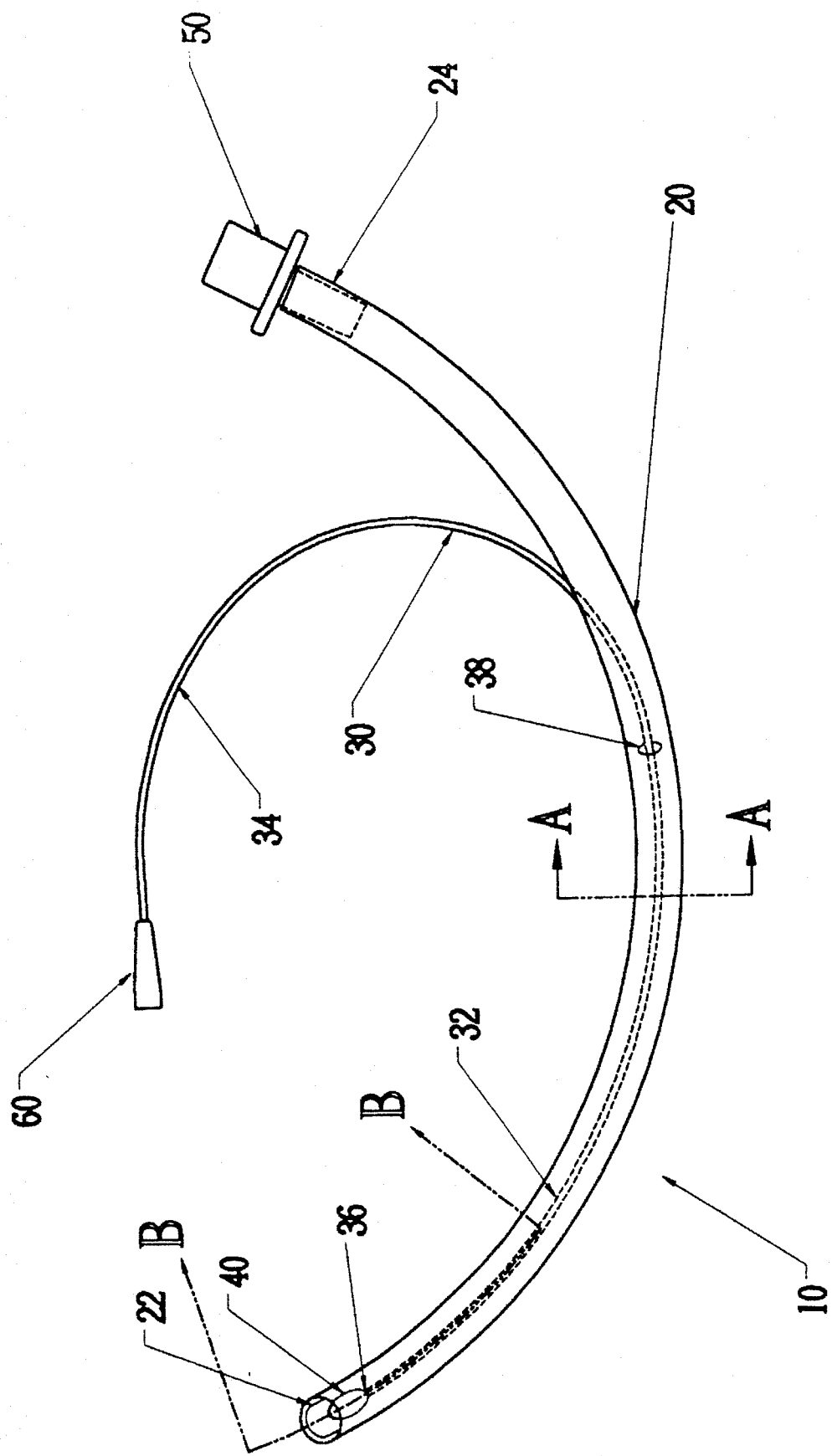
FIG. 1 is a plan view of an endotracheal tube according to one embodiment of the present invention.
Figure 4:
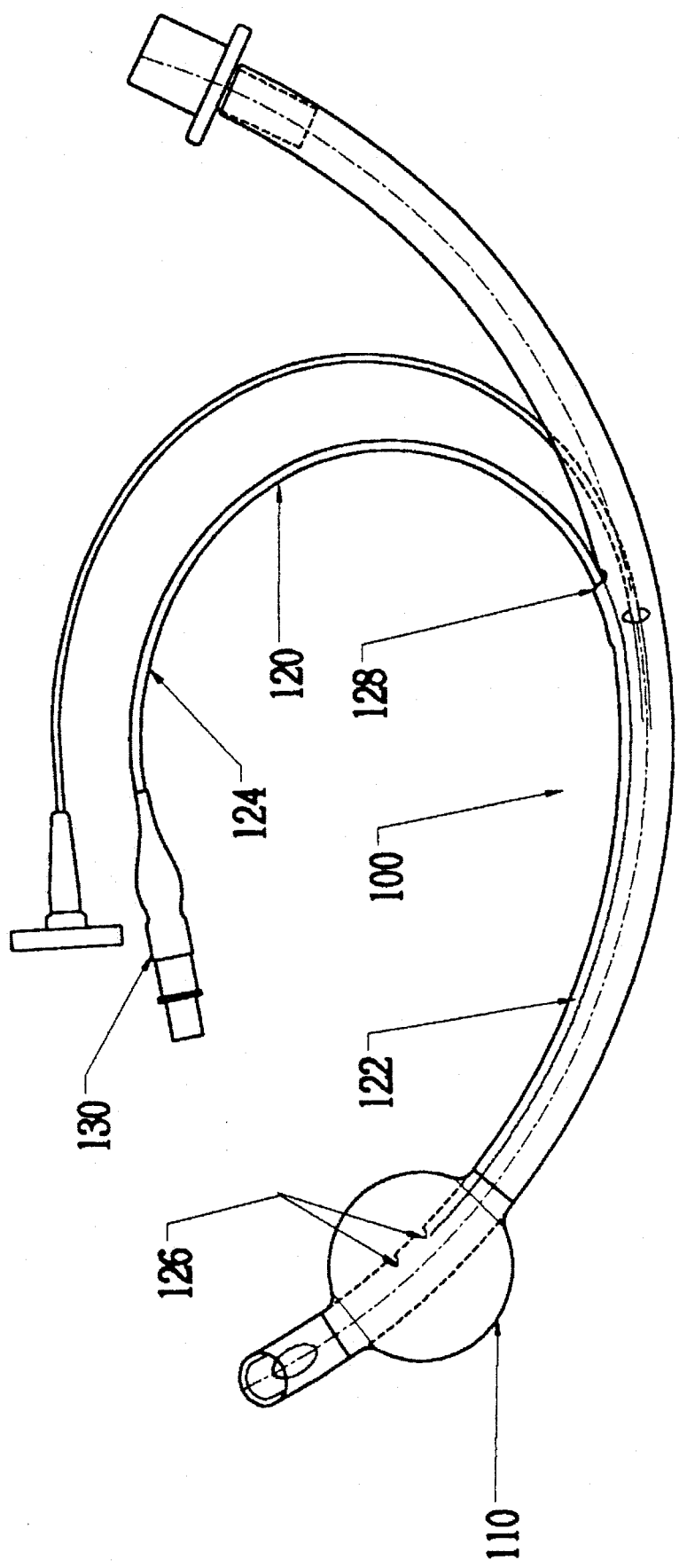
FIG. 4 is a plan view of an endotracheal tube according to another embodiment of the present invention.

The present invention will now be described in detail by reference to the drawing figures, wherein like parts are indicated by like reference numerals.

FIG. 1 shows an endotracheal tube, generally designated by reference numeral 10, including a main tube 20, and a delivery lumen 30, formed within the wall of the main tube 20. Near the distal end 22, of main tube 20, a perforation 40, is formed through the wall of the main tube 20. In a preferred embodiment, perforation 40, is a Murphy eye. As shown in FIG. 1, the proximal end 24, is connected to a standard connection piece 50.

The delivery lumen 30, includes a first portion 32, formed within the wall of main tube 20, and a second portion 34, extending from the first portion 32, to the exterior of main tube 20. In a preferred embodiment, the first portion 32, of delivery lumen 30, is extruded at the same time as main tube 20, and has an exit port 36, located at the proximal side of perforation 40, and an entrance port 38, formed through the exterior wall of main tube 20. The second portion 34, of delivery lumen 30, comprises a pharmaceutical tube which may be inserted into entrance port 38, to form a continuous lumen with first portion 32, of the delivery lumen 30. The second portion 34, of the delivery lumen 30, also includes a standard injection attachment 60, attached to the proximal end. Injection attachment 60, may have a diaphragm through which a hypodermic needle can be inserted to deliver various medicant through the delivery lumen 30, and out the exit port 36, to a patient's lungs.

FIG. 2 is a cross-sectional view of the endotracheal tube 10, taken along section A—A of FIG. 1, showing the delivery lumen 30, formed within the wall of the main tube 20.

The main tube 20, may be formed of any suitable material which provides enough stiffness to allow easy insertion into the trachea of the patient, and enough flexibility to avoid undue stress and damage to the trachea. For example, the main tube 20, may be advantageously formed of flexible plastic materials, such as plasticized polyvinyl chloride, polyurethane or silicone. It is also advantageous to use a material which allows preforming of the endotracheal tube, so as to better conform to the shape of a patients trachea when in place, i.e. in a generally arcuate shape.

The second portion 34, of delivery lumen 30, may also be advantageously formed of flexible materials, such as plasticized polyvinyl chloride, polyurethane or silicone. Materials having greater flexibility can be used for the second portion 34, to allow for ease of use.

The main tube 20, is preferable formed by an extrusion technique, although one skilled in the art will recognize that other methods of manufacture can also be carried out. As noted above, the first portion 32, of delivery lumen 30, may be advantageously formed during the extrusion process used to form main tube 20. The perforation 40, may then be made through the wall of main tube 20, so as to intersect the first portion 32, of delivery lumen 30, and thus establish exit port 36.

As will further be understood by one skilled in the are, endotracheal tubes will vary in size in order to accommodate different patients and clinical needs. However, a typical endotracheal tube will have an inside diameter for the main tube 20, of about 2.5 to 13.0 mm, and a length of about 13 inches. The delivery lumen should be large enough to allow for injection of medicant to the patient but small enough so as not to impinge on the main lumen and to allow for more accurate metering of the injected medicant. In particular, for an endotracheal tube having an inside diameter of about 8.0 mm, the delivery lumen may have a diameter of about 1.0 to 1.5 mm.

FIG. 3 is an expanded cross-sectional view of the distal end of an endotracheal tube according to the present invention taken along section B—B of FIG. 1. FIG. 3 shows in particular how medicant may be delivered through the delivery lumen 30. In particular, medicant may be injected through the injection attachment 60, and through the delivery lumen 30. The medicant exit through the exit port 36, as a single stream, generally designated by the arrowed line 70. The single stream 70, then impacts against the distal edge 42, of the perforation 40, and is split into two streams, 72A and 72B. The stream 72A, is diverted through the perforation 40, and is generally administered to one lung of the patient. The stream 72B, is diverted to the interior of main tube 20, and exits through the distal end 22, and is generally administered to the other lung of the patient. In this way, it is possible to deliver medicant to both lungs of the patient simultaneously.

The perforation 40, may have any suitable shape which accomplishes the above described function of diverting or splitting the medicant stream. In a preferred embodiment, the perforation 40, is a standard Murphy eye of normal configuration, size and shape.

The present invention takes advantage of the typical construction of endotracheal tubes, which include Murphy eyes, as well known in the art. In particular, the process described above by which a single medicant stream is split into two streams is made possible by the inclusion of the perforation. The splitting of the medicant stream makes it possible to administer the medicant to both lungs of the patient simultaneously, using the distal opening and the perforation as separate exit ports.

In prior art devices, the delivery lumen is not aligned with the perforation. An exit port for the delivery lumen is formed through the interior wall of the main tube by stripping away a portion of the interior wall and forming an hole intersecting the delivery lumen. There are several disadvantages related to this method, primarily related to the necessity of manual labor to accomplish the stripping. Variations in the stripping pressure and length will create variance in the spray pattern of the delivered drug, making such pattern unpredictable and unreproducible.

According to the present invention, the perforation 40, is punched through the main tube 20, following extrusion, in such a manner as to intersect the delivery lumen 30, and thereby form the exit port 36. Creating the exit port 36, in this manner provides more consistent and reproducible results. In particular, the spray pattern can be accurately measured and consistently reproduced.

Further, formation of the perforation 40, by a punching method provides the clinical advantages noted above relating to the splitting of the medicant stream. In particular, with careful selection of the dimensions of the perforation 40, and delivery lumen 30, allow relatively low medicant injection pressure to be utilized. The impact of the medicant stream 70, against the distal edge of the perforation 40, results in an effective atomizing of the medicant without having to use high injection rates or high airflow. This spray effect is consistent over a reasonable range of exit port 36, angular displacements from the center of the proximal end of the perforation 40. It should be noted that the atomization and splitting effect of the present invention can be achieved for any angular displacement, the only requirement being that the punched perforation 40, intersects the delivery lumen 30. Also, as noted above, the splitting of the medicant stream 70, makes it possible to administer the medicant to both lungs simultaneously. Preferably, the perforation 40, and delivery lumen 30, are provided in such a way that approximately equal amounts of medicant are administered to each lung.

There are several factors which effect the ability to administer medicant equally to each lung, such as patient position, endotracheal tube position, breathing cycle, injection pressure, etc. However, it is believed that the endotracheal tube design according to the present invention minimizes these effects and provides consistent results.

As already noted, the size and shape of the perforation 40, is important to achieving the desired spray effect. The following experiment was carried out to determine the effect of various configurations of the perforation 40.

EXPERIMENT I

Three groups of 7.0 mm endotracheal tubes having drug delivery lumens were made and Murphy eyes were punched therethrough as indicated below. Each of the tubes tested was were tailed with a 5 French tail and finished with a hooded Murphy tip.

Group A - punched with a 7.0 mm ANSI Standard Z-79 Murphy eye punch.

Group B - punched with a 3.0 mm ANSI Standard Z-79 Murphy eye punch.

Group C - punched with a 4.5 mm ANSI Standard Z-79 Murphy eye punch, perpendicular to its normal orientation.

The above tubes were compared to a standard design which included a straight magill tip and a drug delivery lumen exit port formed by a stripping of the inside wall of the main lumen. The drug delivery lumen was tailed with an 8 French tail.

Spray patterns for each of the above tubes were observed and photographed with the following results.

The standard design showed a fairly regular straight spray aligned with the axis of the tube. Some variability in direction was observed which can be attributed to manufacturing variability. However, there was very little variability in character of spray.

The tubes of Group A produced a straight stream which sometimes followed the tube axis, and other times was directed at an angle through the eye.

Group B tubes produced a spray which tended to exit through the eye at about a right angle to the surface.

The Group C tubes provided results in which the spray would split, about half exiting through the eye and the other half through the main lumen. The angle between the two spray streams varied from about '90° to about 150°.

The above experiment provides evidence that the shape and size of the eye will effect the spray pattern. The Group A tubes provided an acceptable spray pattern which could be modulated with ventilatory timing. The Group B tubes had eyes which appeared to act as added resistance and restricted the spray spatially. The Group C tubes showed the most spatial dispersion. Overall, very little difference in the actual size of droplets produced by the various tubes was observed.

EXPERIMENT II

Several endotracheal tubes having a drug delivery lumen were extruded using known procedures. A standard Murphy eye was then punched through the wall of the tube so as to intersect the drug delivery lumen. The tubes were tailed with 5 French tails and female luer adapters were attached for testing purposes. The pertinent dimensions were measured including offset or the distance between the longitudinal center of the drug delivery lumen and the longitudinal center of the Murphy eye. The spray characteristics were checked visually by injecting 3 to 4 cc or water from a 5 cc syringe through the drug delivery lumen using reasonable force.

This experiment showed the effect of eye width and offset on the spray pattern. Good dispersion of the spray was achieved over a wide range of tube characteristics. This experiment showed that offset was not determinative of achieving a spray pattern, but confirmed that the most important requirement was that the Murphy eye intersect the delivery lumen.

FIG. 4 is a plan view of an endotracheal tube according to another embodiment of the present invention. In particular, FIG. 4 shows an endotracheal tube, generally designated by reference numeral 100, which includes an inflatable cuff 110, and an inflation lumen 120. The inflation lumen 120, includes a first portion 122, formed within the wall of the endotracheal tube 100, and a second portion 124, extending from the first portion 122, to the exterior of endotracheal tube 100. The first portion 122, of inflation lumen 120, includes an exit port 126, formed through the exterior wall of endotracheal tube 100, and in communication with the interior of cuff 110, and an entrance port 128, formed through the exterior wall of endotracheal tube 100 near the proximal end thereof. The second portion 124, of inflation lumen 120, comprises a flexible tube which may be inserted into entrance port 128, to form a continuous lumen with first portion 122, of the inflation lumen 120. The second portion 124, of the inflation lumen 120, also includes a standard inflation attachment 130, attached to the proximal end.

Aside from the features described above, the endotracheal tube 100, is identical in design to the endotracheal tube 10, described in FIG. 1. The inflation lumen 120, is preferable formed during the extrusion process of endotracheal tube 100. The cuff 110, may be selectively inflated to secure the endotracheal tube 100, once it is properly placed within the trachea of a patient. In a preferred embodiment, the inflation lumen 120, is formed at a position spaced apart from the position of the drug delivery lumen, so that the perforation punching operation does not intersect the inflation lumen 120.

It should also be noted that further functional lumens can be included in the endotracheal tube without departing from the general nature of the present invention. For example, an irrigation lumen for removing accumulated secretions from the tracheal bronchial tree, or a monitoring lumen for monitoring airway pressure or heart sounds, may be included.

As already discussed, the present invention provides several advantages, which are summarized below.

Because the present invention utilizes a separate delivery lumen, there is no need to interrupt ventilation during injection of a medicant. In addition, the separate delivery lumen facilitates measurement of the amount of medicant actually delivered to the lungs, by avoiding absorption of collected secretions and adherence to the walls of the endotracheal tube. Further, the present invention provides a means for atomizing the medicant during delivery, without having to use high medicant injection flow rates or high air flow.

Most importantly, the present invention makes it possible to easily administer medicant simultaneously to both lungs of the patient.

The foregoing has been a description of certain preferred embodiments of the present invention, but is not intended to limit the invention in any way. Rather, many modifications, variations and changes in details may be made within the scope of the present invention.

What is claimed is:

1. A method of delivering medicant simultaneously to both lungs of a patient comprising:

providing an endotracheal tube having a main tube including a proximal end; a distal end; a main lumen extending throughout the main tube; and a wall surrounding said main lumen; a perforation formed through said wall of said main tube near said distal end; a drug delivery lumen formed within said wall of said main tube including an exit port formed at the proximal side of said perforation; and an entrance port formed through the exterior portion of said wall of said main tube; and a flexible tube inserted through said entrance port including an injection lumen which corresponds and connects with said drug delivery lumen; and an injection port formed at a proximal end thereof;

intubating the patient with said endotracheal tube; and injecting liquid medicant through said injection port and through said drug delivery lumen such that said medicant exits from said exit port of said drug delivery lumen in substantially a single steam which then impacts the distal edge of said perforation and is thereby split into two separate atomized portions, and is administered simultaneously to both lungs of the patient.

* * * * *